US011013496B2

(12) United States Patent
Muramatsu et al.

(10) Patent No.: US 11,013,496 B2
(45) Date of Patent: May 25, 2021

(54) ULTRASOUND DIAGNOSTIC APPARATUS

(71) Applicant: Konica Minolta, Inc., Tokyo (JP)

(72) Inventors: Yuki Muramatsu, Hachioji (JP);
Yasuhiro Nakamura, Sagamihara (JP);
Yosuke Kimura, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 812 days.

(21) Appl. No.: 15/798,870

(22) Filed: Oct. 31, 2017

(65) Prior Publication Data
US 2018/0116638 A1    May 3, 2018

(30) Foreign Application Priority Data

Nov. 2, 2016  (JP) .............................. JP2016-214791

(51) Int. Cl.
*A61B 8/00*   (2006.01)
*A61B 8/08*   (2006.01)
*A61B 8/14*   (2006.01)

(52) U.S. Cl.
CPC ................. *A61B 8/56* (2013.01); *A61B 8/14* (2013.01); *A61B 8/5207* (2013.01); *A61B 8/5269* (2013.01); *A61B 8/4444* (2013.01); *A61B 8/4494* (2013.01); *A61B 8/461* (2013.01)

(58) Field of Classification Search
CPC ....... A61B 8/14; A61B 8/4444; A61B 8/4494; A61B 8/461; A61B 8/5207; A61B 8/5269; A61B 8/56
See application file for complete search history.

(56) References Cited

U.S. PATENT DOCUMENTS

2013/0079642 A1* 3/2013 Marshall .................. A61B 8/12
600/463

FOREIGN PATENT DOCUMENTS

JP   2011067518   *  9/2009
JP   2014083155 A   5/2014

* cited by examiner

*Primary Examiner* — Christopher L Cook
(74) *Attorney, Agent, or Firm* — Cantor Colburn LLP

(57) ABSTRACT

An ultrasound diagnostic apparatus includes an ultrasound probe and a display. The apparatus includes a power supply including at least one voltage converting circuit converting input voltage to a predetermined power voltage for output. The voltage converting circuit includes a coil and a switching element performing a switching operation for switching routes of current flowing in the coil in response to a predetermined switching control signal, and the voltage converting circuit outputs the power voltage through the repeated switching operations under supply of the input voltage. The power supply is provided with a plurality of coils, and the coils are disposed such that a leakage magnetic field in a vicinity of an aperture of at least one of the coils is partially negated by a leakage magnetic field from one or more of the other coils.

12 Claims, 7 Drawing Sheets

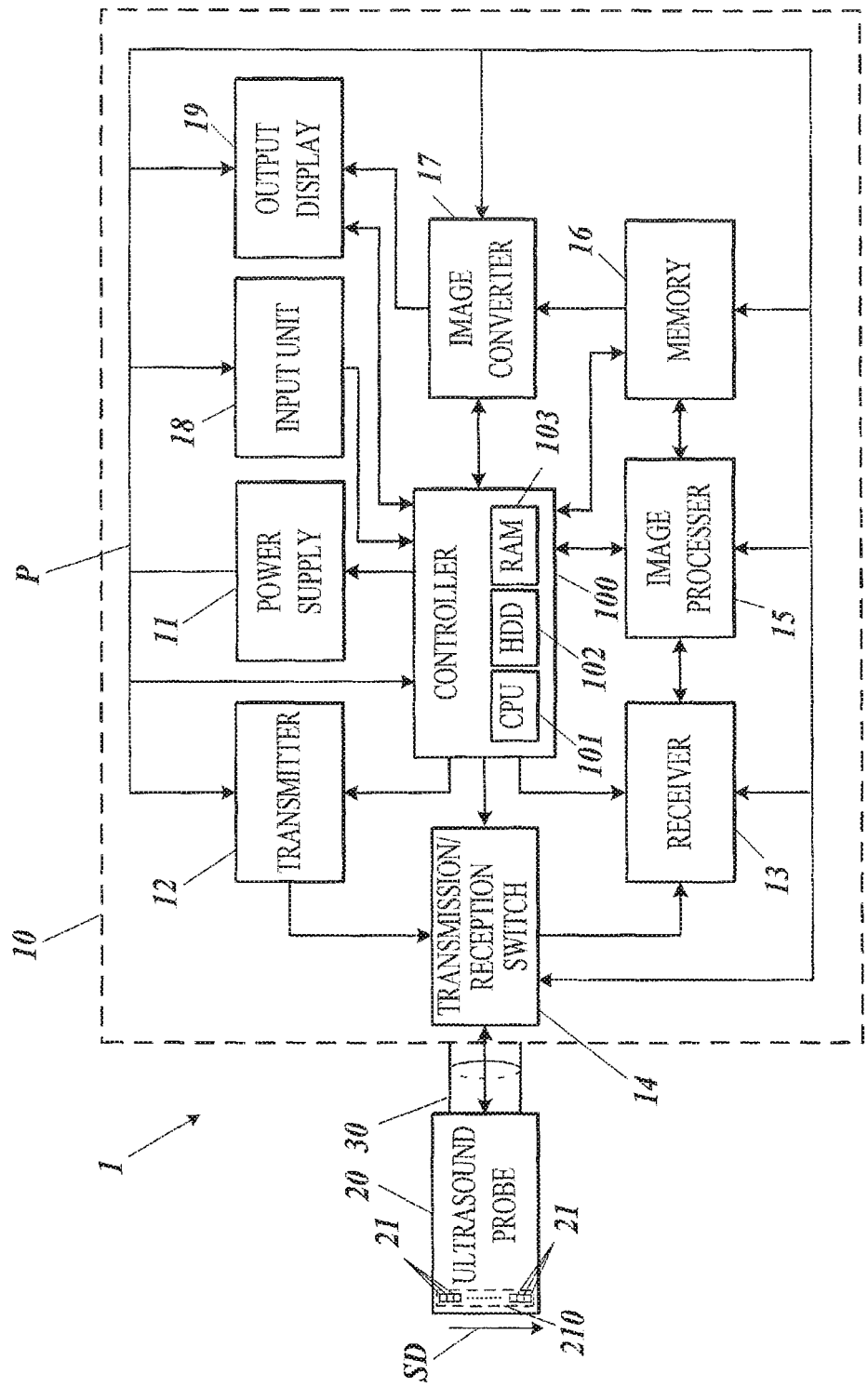

United States Patent US 11,013,496 B2

ULTRASOUND DIAGNOSTIC APPARATUS

CROSS REFERENCES TO RELATED APPLICATIONS

The present invention claims priority under 35 U.S.C. § 119 to Japanese Patent Application 2016-214791, filed Nov. 2, 2016, the entire contents of which being incorporated herein by reference.

BACKGROUND

Technological Field

The present invention relates to an ultrasound diagnostic apparatus.

Description of the Related Art

A traditional ultrasound diagnostic apparatus emits ultrasound from an ultrasound probe toward a subject of interest, receives the reflected waves from the subject, processes the received signals, generates an ultrasound image corresponding to the internal structure of the subject, and displays the ultrasound image on a display. The ultrasound image provides diagnostic information of the internal structure. Such an ultrasound diagnostic apparatus is also used as a noninvasive diagnostic device for medical care for humans.

This type of ultrasound diagnostic apparatus includes a power supply having multiple voltage conversion circuits converting an input voltage into a predetermined power voltage and outputting it. The power voltage generated at the power supply drives individual components in the ultrasound diagnostic apparatus. A general type of voltage conversion circuit for such a power supply switches the routes of the current flowing in a coil at a predetermined frequency with a switching element and thereby converts the input voltage.

Unfortunately, such an ultrasound diagnostic apparatus has the drawback that the coils of the voltage conversion circuits generate a magnetic field which leaks out of the coils, and the induced electromotive force of the leakage magnetic field generates a noise in the received ultrasound signals, decreasing the quality of an ultrasound image.

To solve such a drawback, Japanese Unexamined Patent Application Publication No. 2014-83155 discloses a technique on an operation at different frequencies of multiple voltage conversion circuits for spreading the frequency bandwidth of noises, thereby maintaining the image quality.

Unfortunately, the traditional technique described above cannot necessarily operate the voltage conversion circuits at optimal frequencies, resulting in low power conversion efficiency in the power supply. Another problem is the operation of multiple voltage conversion circuits at different frequencies, complicating the control of the power supply.

SUMMARY

An object of the present invention is to provide an ultrasound diagnostic apparatus that can maintain proper power supply efficiency, while preventing decrease in quality of an ultrasound image.

According to an aspect of the present invention there is provided an ultrasound diagnostic apparatus including an ultrasound probe emitting ultrasound toward a subject and receiving reflected ultrasound from the subject and a display for displaying an ultrasound image in response to a signal received by the ultrasound probe, the apparatus including: a power supply including at least one voltage converting circuit converting input voltage to a predetermined power voltage for output, wherein, the voltage converting circuit includes a coil and a switching element performing a switching operation for switching routes of current flowing in the coil in response to a predetermined switching control signal, and the voltage converting circuit outputs the power voltage through the repeated switching operations under supply of the input voltage, wherein the power supply is provided with a plurality of coils, and the coils are disposed such that a leakage magnetic field in a vicinity of an aperture of at least one of the coils is partially negated by a leakage magnetic field from one or more of the other coils.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

FIG. 2 is a block diagram illustrating major functional components of the ultrasound diagnostic apparatus.

DETAILED DESCRIPTION OF THE EMBODIMENTS

The embodiments of an ultrasound diagnostic apparatus according to the present invention will now be described in reference to the accompanying drawings.

Figure 1:
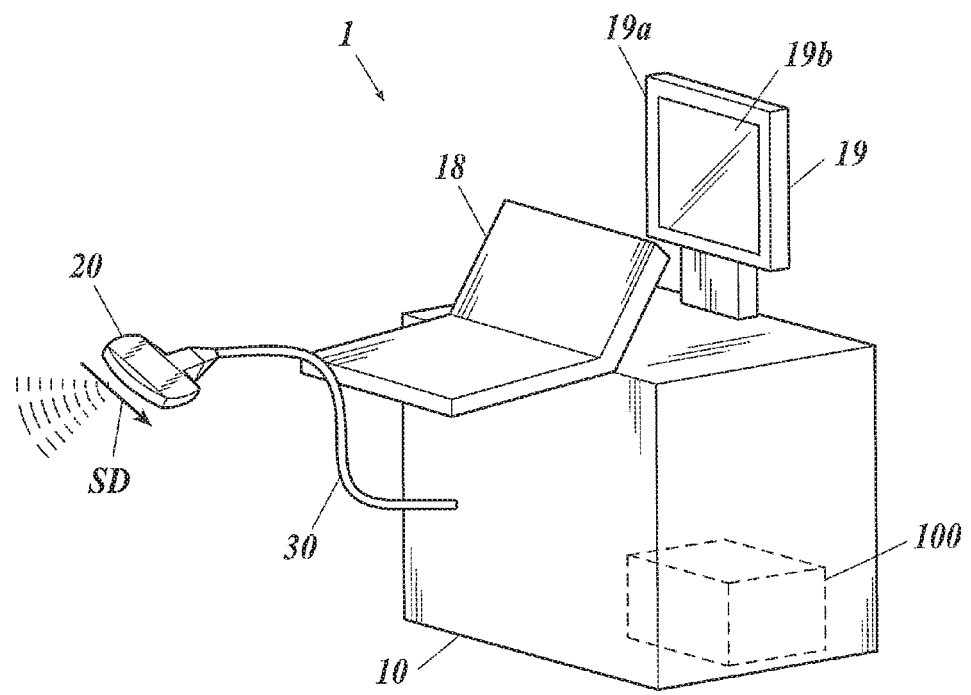
FIG. 1 is a schematic view of an ultrasound diagnostic apparatus.

FIG. 1 is a schematic view of an ultrasound diagnostic apparatus 1 according to an embodiment of the present invention.

FIG. 2 is a block diagram illustrating major functional components of the ultrasound diagnostic apparatus 1.

As illustrated in FIG. 1, the ultrasound diagnostic apparatus 1 includes an ultrasound diagnostic apparatus main body 10 and an ultrasound probe 20 connected with the ultrasound diagnostic apparatus main body 10 via a cable 30. The ultrasound diagnostic apparatus main body 10 includes, for example, a controller 100, an input unit 18, an output display 19 having a display 19a and a touch panel 19b. The controller 100 outputs driving signals to the ultrasound probe 20, causes it to output ultrasound in response to the input operation by an operator through input devices, such as a keyboard or a mouse of the input unit 18 and the touch operation by the operator with the touch panel 19b on the output display 19, receives signals regarding ultrasound reception from the ultrasound probe 20, processes the signals and allows, for example, the results of the process to appear on the display 19a if necessary.

As illustrated in FIG. 2, the ultrasound diagnostic apparatus main body 10 includes, for example, the controller 100, a power supply 11, a transmitter 12, a receiver 13, a transmission/reception switch 14, an image processor 15, a memory 16, an image converter 17, an input unit 18, and the output display 19.

The controller 100 includes, for example, a central processing unit 101 (CPU), a hard disk drive 102 (HDD), and a random access memory 103 (RAM). The CPU 101 retrieves various programs stored in the HDD 102 and deploys them in the RAM 103 to comprehensively control the operation of individual components in the ultrasound diagnostic apparatus 1 under instructions of the deployed programs. The HDD 102 stores, for example, control programs and various application programs operating the ultrasound diagnostic apparatus 1, various setting data, and image files generated in the ultrasound diagnostic apparatus 1. These programs and setting data may be stored not only in the HDD 102 but also, for example, in an auxiliary storage device including a non-volatile memory such as a flash memory in a readable, writable, and updatable manner. The RAM 103 is a volatile memory such as a static random access memory (SRAM) and dynamic random access memory (DRAM) and provides some memory spaces for operation to the CPU 101 and stores temporary data.

The power supply 11 is connected with an external alternating current (AC) power supply and includes, for example, an AC-DC converter converting the AC voltage from the external AC power supply to a direct current (DC) input voltage, multiple voltage converting circuits 111 (in FIG. 3A) converting the input voltage generated in the AC-DC converter to a predetermined DC power voltage, and an oscillation circuit 112 (in FIG. 3A) used for operation of the voltage converting circuits 111. The voltage converting circuits 111 operate in response to the control signals from the controller 100, generate different power voltages and output them through voltage supply lines P. In the present embodiment, the AC-DC converter generates an input voltage of 5 V, and then the voltage converting circuits 111 each convert (step down) the input voltage to a predetermined output power voltage ranging from 1 V to 3.3 V. The multiple power voltages generated in the power supply 11 are supplied to the respective components in the ultrasound diagnostic apparatus main body 10, such as the controller 100, the transmitter 12, the receiver 13, the transmission/reception switch 14, the image processor 15, the memory 16, the image converter 17, the input unit 18, and the output display 19, through the voltage supply lines P. One or more predetermined power voltages of multiple power voltages necessary for operation are input to the respective components in the ultrasound diagnostic apparatus main body 10. It should be noted that the power supply 11 may convert a DC voltage from a battery or cells provided in the ultrasound diagnostic apparatus 1 to multiple power voltages.

The transmitter 12 outputs pulsed signals (driving signals) to be supplied to the ultrasound probe 20 in response to the control signals from the controller 100 and causes the ultrasound probe 20 to generate ultrasound. The transmitter 12 includes, for example, a clock generating circuit, a pulse generating circuit, a pulse-width setting unit, and a delay circuit. The clock generating circuit generates clock signals that determine the timing for transmitting pulsed signals and transmission frequencies. The pulse generating circuit generates a bipolar rectangular pulsed waves having a preset voltage amplitude in a predetermined cycle. The pulse-width setting unit determines the pulse width of the rectangular pulsed waves output from the pulse generating circuit. The rectangular pulsed waves generated by the pulse generating circuit are distributed to different wiring routes for transducers 21 in the ultrasound probe 20 before or after being input into the pulse-width setting unit. The delay circuit delays the output of the generated rectangular pulsed waves by the delay time set for each wiring route depending on the timing of the transmission of the rectangular pulsed waves to each transducer 21. The transmitter 12 includes a semiconductor integrated circuit such as a field-programmable gate array (FPGA).

The receiver 13 accepts signals input from the ultrasound probe 20 under an instruction of the controller 100. The receiver 13 includes, for example, an amplifier, an A/D converter, and a phase regulating adder. The amplifier amplifies the received analog signals corresponding to the ultrasound received at each transducer 21 in the ultrasound probe 20 at a predetermined amplification factor. The A/D converter converts the amplified signals to digital data at a predetermined sampling frequency. The phase regulating adder designates delay times for wiring routes corresponding to the respective transducers 21 for the digital signals, regulates the time phases, and adds the phase-regulated signals, thereby generating sound ray data. The receiver 13 may include a semiconductor integrated circuit such as a FPGA.

The transmission/reception switch 14 switches the signal transmission so as to cause the transmitter 12 to transmit driving signals to the transducers 21 for generating the ultrasound from the transducers 21 under an instruction of the controller 100, and to cause the receiver 13 to output the received signals for receiving signals corresponding to the ultrasound from the transducers 21.

The image processor 15, independent of the CPU 101 in the controller 100, performs arithmetic processes for generating ultrasound image data (diagnostic images) from the received ultrasound. The ultrasound image data may include, for example, image data to appear on the output display 19 substantially in real time, a series of its video data, and snapshot data. It should be noted that the CPU 101 may be configured to perform the arithmetic processes. The image processor 15 includes a semiconductor integrated circuit, for example, a FPGA and/or digital signal processor (DSP). The image processor 15 and the receiver 13 may also be consolidated into a single semiconductor integrated circuit.

The memory 16 is a volatile memory such as a DRAM. Alternatively, the memory 16 may be a high-rate rewritable non-volatile memory of various types. The memory 16 stores ultrasound image data processed at the image processor 15 for display in real time in the unit of frames. The image data stored in the memory 16 is retrieved under an instruction of the controller 100, transmitted to the image converter 17 and output to the exterior of the ultrasound diagnostic apparatus 1 through a communication unit (not shown).

The image converter 17 is provided between the memory 16 and the output display 19, converts image data stored in the memory 16 to image data conforming to the displaying mode of the display 19a in the output display 19 (television system mode, for example) and outputs the converted image data to the output display 19. Specifically, the image converter 17 converts the scanning format of the image data to that of the display 19a (interlace and progressive techniques, for example). The image converter 17 includes a semiconductor integrated circuit such as a DSP. It should be noted that the image converter 17 may be omitted if the image processor 15 can generate the image data conforming to the displaying mode of the display 19a.

The input unit 18 includes a push button switch, toggle switch, keyboard, mouse or track ball, or a combination thereof that converts the input operation by the operator to operation signals and outputs them to the controller 100.

The display 19a of the output display 19 may be any display, for example, a liquid crystal display (LCD), organic electro-luminescent (EL) display, inorganic EL display, plasma display, or cathode ray tube (CRT) display, and a driver for the display. The display 19a generates driving signals for pixels in the screen in response to the control signals output from the CPU 101 and the image data supplied from the image converter 17 and displays, for example, ultrasound images on the screen based on menus and statuses associated with the ultrasound diagnostics, operation buttons indicating the object of the touch operation to be accepted by the touch panel 19b, and the received ultrasound.

The touch panel 19b of the output display 19 is of an electrostatic capacitive type provided on the screen of the display 19a. The touch panel 19b detects touch operation based on a change in electrostatic capacitance between the surface and the inner conductive film of the touch panel 19b when the operator touches the surface with, for example, fingers, and outputs the operation signals indicating the detected position (coordinates) to the controller 100. It should be noted that any other technique than the capacitive sensing mode may be used for the touch panel 19b. Examples of such a mode includes but is not limited to resistive membrane and electromagnetic induction modes.

The input unit 18 and the output display 19 may be integrated with the casing of the ultrasound diagnostic apparatus main body 10 and may be connected to the exterior of the ultrasound diagnostic apparatus main body 10 with, for example, a USB cable. When the ultrasound diagnostic apparatus main body 10 includes an input terminal and an output terminal, these terminals may be connected with common peripheral devices for operation and display.

In FIG. 1, the input unit 18 and the output display 19 are separately provided. Alternatively, they may be integrated. For example, the casing of the output display 19 including the display 19a and the touch panel 19b may include various operation buttons and track balls for the input unit 18.

The ultrasound probe 20 oscillates ultrasound (on the order of 1 to 30 MHz in this case) and transmits (emits) them toward a subject such as a living body. The ultrasound probe 20 also serves as a sonic sensor receiving the waves (echoes) reflected by the subject among the transmitted ultrasound and converting them to electric signals. The ultrasound probe 20 includes a transducer array 210 composed of multiple transducers 21 transmitting and receiving ultrasound. Each of the transducers 21 in the transducer array 210 includes a piezoelectric device having a piezoelectric element and electrodes on the two edges of the piezoelectric element. Charges are induced by deformation (telescopic motion) of the piezoelectric element through variations in acoustic pressure of the received ultrasound.

The ultrasound probe 20 according to the present embodiment transmits ultrasound from some of the transducers 21 in the transducer array 210 in response to pulsed signals from the transmitter 12 and shifts the transducers 21 transmitting ultrasound every time the ultrasound is generated, thereby performing scanning in the scanning direction SD parallel to the transducer array. In the present embodiment, the ultrasound probe 20 uses a convex electronic scanning technique that forms a sector-shaped area in which ultrasound is transmitted at different timings. It should be noted that the ultrasound probe 20 may employ any electronic scanning technique, for example, electronic linear or electronic sector scanning, or any mechanical scanning technique, for example, linear, sector, arc, or radial scanning.

The cable 30 includes a connector 30a (in FIG. 7) used to connect with the ultrasound diagnostic apparatus main body 10 at one end. The ultrasound probe 20 is configured to be connected with and disconnect from the ultrasound diagnostic apparatus main body 10 through the cable 30.

The configuration and geometry of the voltage converting circuits 111 in the power supply 11 of the ultrasound diagnostic apparatus 1 will now be described in detail.

Figure 3A:
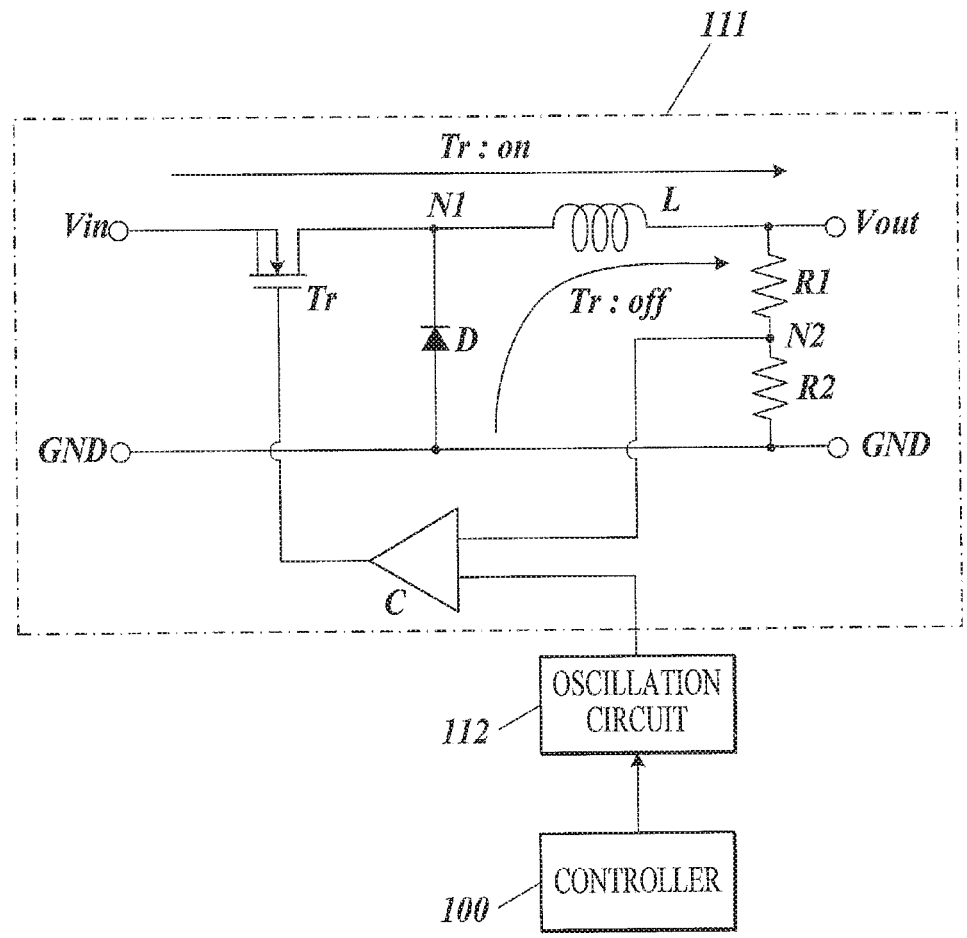
FIG. 3A illustrates the configuration and the operation of a voltage conversion circuit provided in a power supply.

FIG. 3A illustrates the configuration and the operation of the voltage converting circuit 111 in the power supply 11.

As illustrated in FIG. 3A, the voltage converting circuits 111 include a transistor Tr (a switching element) connected with a voltage input terminal Vin to receive the input voltage from the AC-DC converter, a coil L between the transistor Tr and a voltage output terminal Vout, a diode D between a ground terminal GND at ground potential and a node N1 of the transistor Tr and the coil L and, resistors R1 and R2 in series disposed between the voltage output terminal Vout and the ground terminal GND, and a comparator C having a first input terminal connected with a node N2 of the resistors R1 and R2 and having an output terminal connected with the gate of the transistor Tr. The voltage converting circuit 111 may be composed of a single electronic component including packaged individual elements. Alternatively, the voltage converting circuit 111 may be composed of a combination of discrete components mounted on a circuit board.

The power supply 11 includes an oscillation circuit 112 that oscillates to output sinusoidal waves under an instruction of the controller 100. The sinusoidal waves from the oscillation circuit 112 are sent to a second input terminal of the comparator C.

The comparator C alternately outputs an on-voltage turning on the transistor Tr and an off-voltage turning off the transistor Tr depending on the comparative results between the voltage of the sinusoidal waves from the oscillation circuit 112 and the shunt voltage at the node N2 generated from the voltage of the voltage output terminal Vout through the resistors R1 and R2. Thus, the signals output from the comparator C are switching signals controlling the operation of the transistor Tr. The comparator C, the oscillation circuit 112 and the controller 100 define a power controller.

The voltage converting circuit 111 switches the route of the current flowing in the coil L with the transistor Tr. When the transistor Tr is an ON state (activated), current flows from the voltage input terminal Vin to the coil L. When the transistor Tr is an OFF state (inactivated), current flows from the diode D to the coil L due to the induced electromotive force of the coil L. Since the node N1 is at ground potential through the diode D in this state, the voltage at the voltage output terminal Vout drops. The voltage converting circuit 111 repeats such a switching operation at a predetermined frequency, thereby stepping down the input voltage in proportion to the ratio of the OFF period to the total period of the transistor Tr (duty ratio). Power voltage is thereby generated, which is output from the voltage output terminal Vout.

Figure 3B:
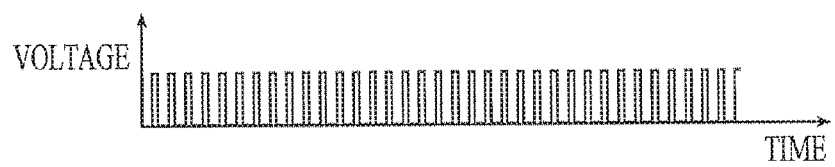
FIG. 3B illustrates an exemplary control signal output from a comparator.

FIG. 3B illustrates exemplary switching control signals output from the comparator C. As illustrated in this drawing, the comparator C outputs rectangular switching signals at a switching frequency corresponding to the oscillating frequency from the oscillation circuit 112. In this context, the duty ratio of the switching signals or the ratio of the period of the OFF-voltage output in the cycles of the rectangular waves converges to a predetermined value corresponding to the resistances of the resistors R1 and R2 through feedback of the potential at the node N2 to the input of the comparator C. In the voltage converting circuits 111, the resistances of the resistors R1 and R2 are determined such that the input voltage is stepped down to a desired power voltage and output from the voltage output terminal Vout at the predetermined duty ratio of the switching control signals.

In the power supply 11, the number of the voltage converting circuits 111 equals that of the power voltages to be output. The common oscillation circuit 112 supplies the voltage converting circuits 111 with the same sinusoidal waves. In other words, the voltage converting circuits 111 are identical in the switching frequency and the phase of the circuit and operate at different duty ratios depending on the resistances of the resistors R1 and R2. The voltage converting circuits 111 thus operates such that the ON or OFF periods of the transistors Tr at least partially overlap with each other.

The coil L generates internal and external magnetic fields in a direction corresponding to that of the current flowing in the coil L (hereinafter, the magnetic field generated outside the coil L is referred to as a leakage magnetic field). Since the magnitude of the current flowing in the coil L fluctuates according to the oscillating frequency of the oscillation circuit 112, the magnitude of leakage magnetic field from the coil L also fluctuates according to the oscillating frequency. Because such a fluctuating leakage magnetic field generates a noise in ultrasound signals from the ultrasound probe 20 due to their induced electromotive force, it is desirable to reduce the leakage of the magnetic field as much as possible.

Some or all of the voltage converting circuits 111 are thus disposed such that leakage magnetic fields from the coils L are offset in the power supply 11 of the ultrasound diagnostic apparatus 1 according to the present embodiment.

Figure 4:
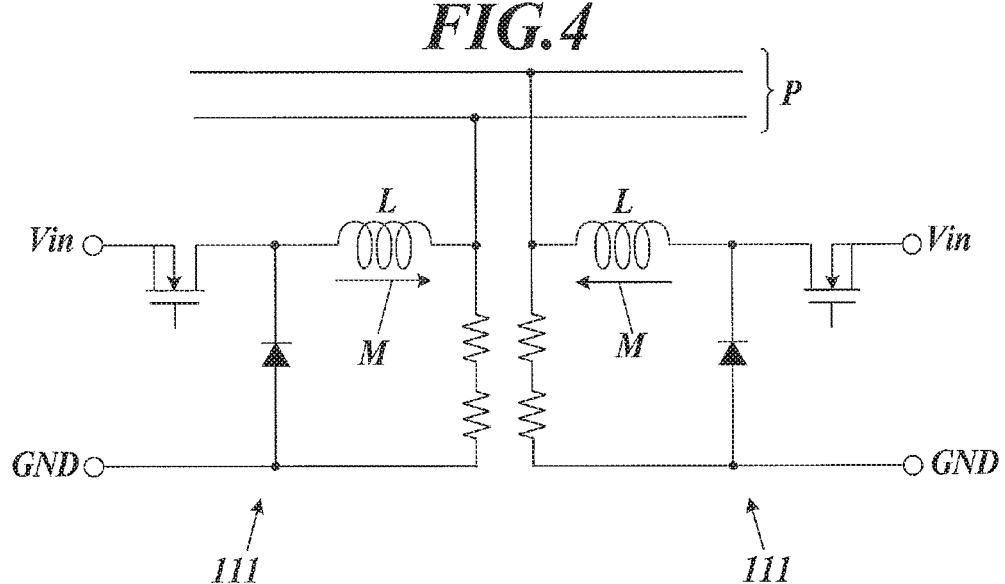
FIG. 4 illustrates an exemplary layout of the voltage conversion circuits.

FIG. 4 illustrates an exemplary layout of the voltage converting circuits 111 according to the present embodiment. FIG. 4 depicts typical directions M of the magnetic fields generated in the center of the coils L.

In FIG. 4 illustrating two voltage converting circuits 111, the direction M of the magnetic field generated by a coil L in one voltage converting circuit 111 is opposite to the direction M of the magnetic field generated by a coil L in another voltage converting circuit 111. One aperture of one coil L faces one aperture of the other coil L. Such a layout enables the leakage magnetic field in the vicinity of the aperture of the one coil L to be partially offset by the leakage magnetic field from the other coil L, thus reducing the leakage magnetic field from the two voltage converting circuits 111 and reducing the noise in the received ultrasound signals. In particular, since the switching frequency and the phase of the circuits is identical between the voltage converting circuits 111 in the present embodiment, the leakage magnetic fields from the coils L are in the same phase and can be effectively offset.

Figure 5A:
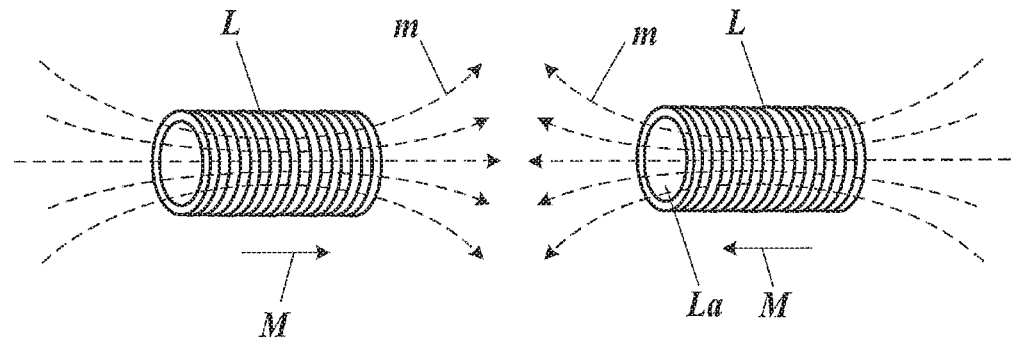
FIG. 5A illustrates exemplary positional relations of coils relative to one another in the power supply.
Figure 5B:
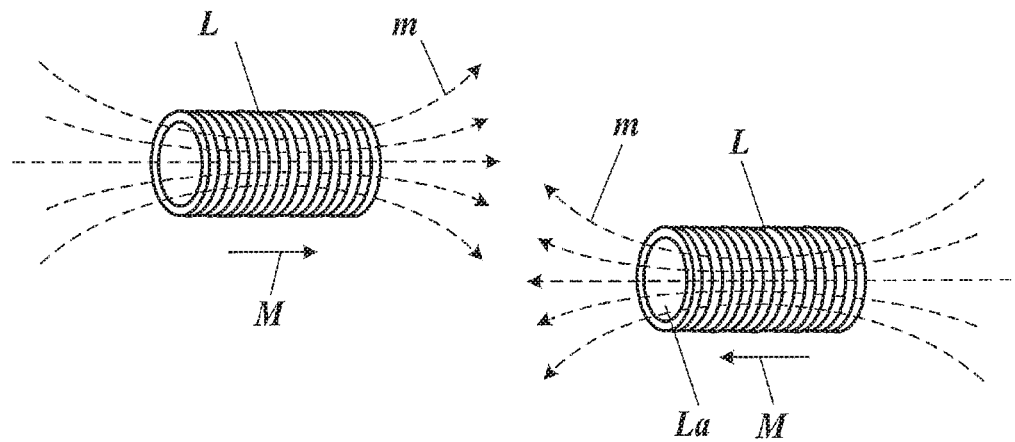
FIG. 5B illustrates exemplary positional relations of the coils relative to one another in the power supply.

FIGS. 5A and 5B illustrate exemplary positional relations of the coils L in the power supply 11.

As illustrated in FIG. 5A, a pair of coils L is disposed such that apertures La of the coils L face each other in the two voltage converting circuits 111, resulting in an effective offset of leakage magnetic fields m in the vicinity of the apertures La. In this context, the aperture La of the coil L denotes the bottom face of a cylindrical space defined by the side surrounded by a wire of the coil L. The vicinity of the aperture La refers to an area having components in which the direction of the leakage magnetic field m from the aperture La of the coil L is in the same direction as the direction M of the magnetic field in the center of the coil L, and the magnitude of the leakage magnetic field m generates a noise substantially impairing the quality of an ultrasound image.

FIG. 5B illustrates the one coil L in FIG. 5A that is shifted such that the apertures La do not face each other in the direction perpendicular to the magnetic fields M. Even if the pair of coils L is disposed in this manner, the leakage magnetic field from the one coil L in the vicinity of the aperture can be partially negated by the leakage magnetic field from the other coil L, reducing the leakage magnetic fields from the two voltage converting circuits 111.

The geometry of the coils L shown in FIGS. 5A and 5B may be replaced with any other one that can partially negate the leakage magnetic field in the vicinity of the aperture of the one coil L with the leakage magnetic field from the other coil L. For example, the magnetic fields M from the one coil L may have a tilt angle to the magnetic field M from the other coil L. The distance between the one coil L and the other coil L may be as short as possible within a range that can at least partially offset the magnitude of the leakage magnetic fields generating a noise in ultrasound receiving signals. The distance between the coils L for offsetting leakage magnetic fields is 10 cm and less, preferably 5 cm and less, and more preferably 2 cm and less.

FIGS. 5A and 5B illustrate the coil L as a cylindrically wound wire. Alternatively, the coil L may have any other shape, for example, prisms such as a quadrangular prism, or may be curved in the longitudinal direction.

Multiple voltage converting circuits 111 may be disposed such that the leakage magnetic field from one of the coils L is partially negated by the leakage magnetic fields from the other coils L.

Figure 6:
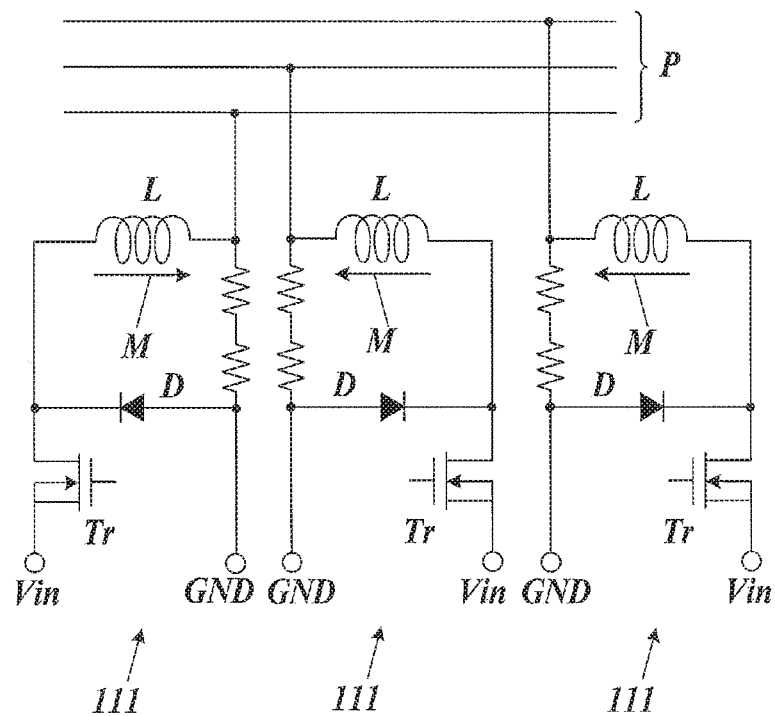
FIG. 6 illustrates an exemplary geometry of three voltage conversion circuits partially offsetting leakage magnetic fields.

FIG. 6 illustrates three voltage converting circuits disposed so as to partially negate leakage magnetic fields.

In FIG. 6, the magnetic field M of the coil L in the left voltage converting circuit 111 is directed to the right, whereas the magnetic fields M in the central and right circuits are directed to the left. These voltage converting circuits 111 include the coils L that are aligned such that the apertures of the coils L face one another. Also in this case, the distance between the coils L offsetting the leakage magnetic fields (in other words, between the left and center coils L, and between the left and right coils L) is 10 cm and less, preferably 5 cm and less, and more preferably 2 cm and less. Such geometry also enables partial offset of the leakage magnetic fields in the vicinity of the aperture of the coil L by the leakage magnetic fields from the other coils L, reducing the leakage magnetic fields from the two voltage converting circuits 111. In particular, a magnetic field generated in the coil L in the left voltage converting circuit 111 on the left larger than those generated in the coils L in the center and right voltage converting circuits 111 in the geometry of FIG. 6 can effectively reduce the leakage magnetic fields.

It should be noted that magnetic fields may be offset between a group of multiple coils L and another group of multiple coils L instead of between a single coil L and multiple coils L.

Figure 7:
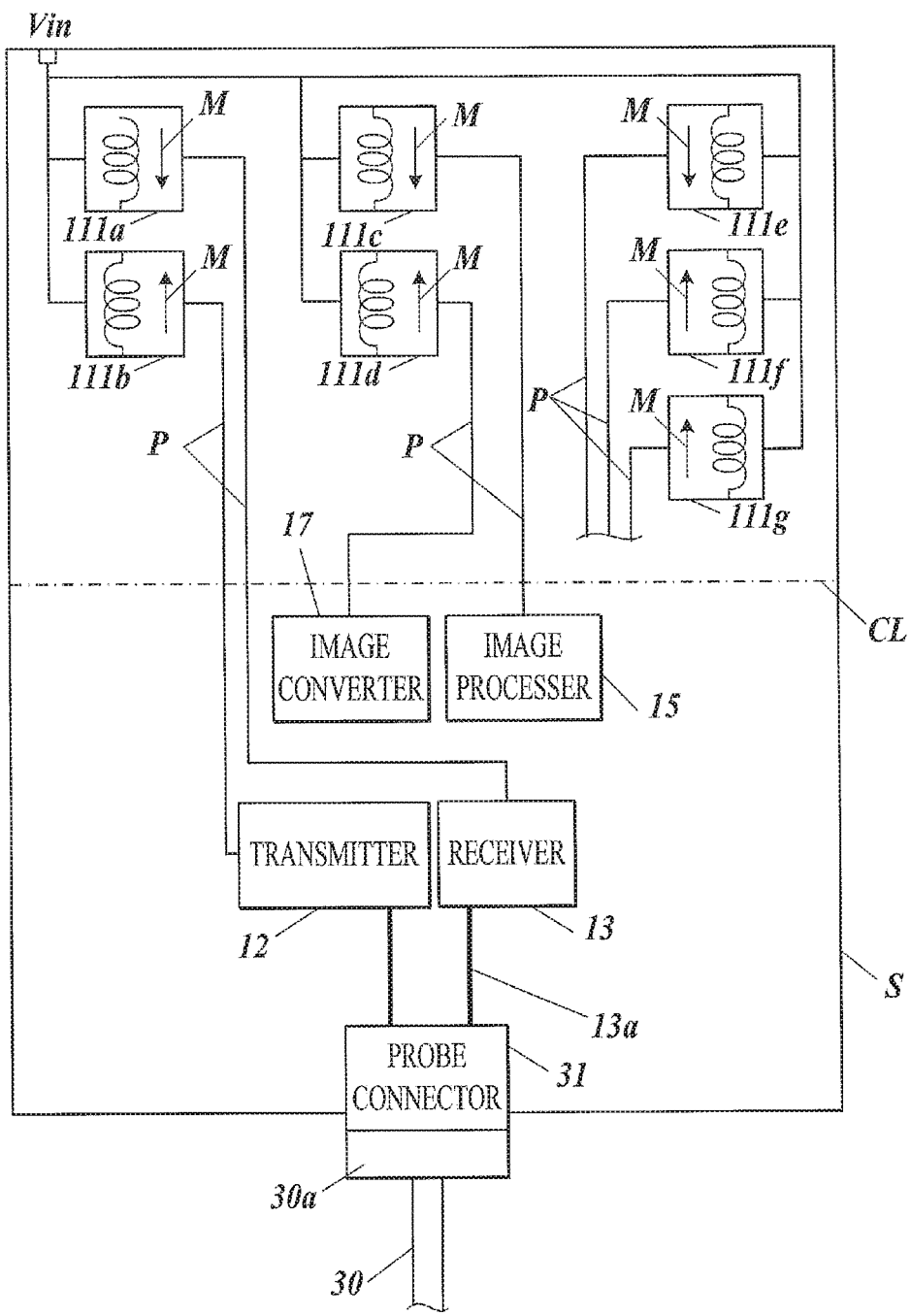
FIG. 7 illustrates an exemplary geometry of the voltage conversion circuits on a board in the ultrasound diagnostic apparatus.

FIG. 7 illustrates an exemplary geometry of the voltage converting circuits 111 on a board S in the ultrasound diagnostic apparatus 1.

In the ultrasound diagnostic apparatus 1 of the present embodiment, seven voltage converting circuits 111 (voltage converting circuits 111a to 111g) independently packaged and mounted on the board S, and the seven voltage converting circuits 111 define a power supply 11. The board S is a circuit board composed of a rectangular plate having sides of about 20 to 30 cm. Each of the voltage converting circuits 111 includes a coil L provided such that the direction M of the magnetic field generated in the coil L is parallel to the board S (in other words, such that the coil L in the longitudinal direction is parallel to the board S). The voltage converting circuits 111a and 111b neighbor each other such that the magnetic fields generated at the coils L are directed to directions M in opposite directions. The voltage converting circuits 111c and 111d neighbor such that the magnetic fields generated at the coils L are directed to directions M in opposite directions. The voltage converting circuits 111e, 111f, and 111g neighbor such that the magnetic fields generated by the coils L are directed to directions M in opposite directions between the voltage converting circuits 111e and 111f and between the voltage converting circuits 111e and 111g.

A transmitter 12, a receiver 13 and an image processor 15 each including a FPGA and an image converter 17 including a DSP are mounted on the board S.

Furthermore, a probe connector 31 for being connected to the connector 30a of the cable 30 is provided at one end of the board S. The probe connector 31 is also connected to both the transmitter 12 and the receiver 13 through lines. Among the lines, a line 13a between the receiver 13 and the probe connector 31 defines a transmission route of ultrasound analog signals received at the ultrasound probe 20.

In FIG. 7, the seven voltage converting circuits 111 included in the power supply 11 are provided such that the leakage magnetic field from the coil L is negated relative to at least one of the other voltage converting circuits 111. Alternatively, some of the voltage converting circuits 111 may be disposed in a position shifted from the other voltage converting circuits 111 where a noise is unlikely to be generated in ultrasound receiving signals (in other words, in a position in which the leakage magnetic fields from the coils L are scarcely offset relative to the other voltage converting circuits 111).

A first voltage converting circuit 111a feeds power voltage to the receiver 13, and a second voltage converting circuit 111b feeds power voltage to the transmitter 12. In this context, the transmitter 12 and the receiver 13 have a relatively high power consumption among individual components in the ultrasound diagnostic apparatus 1 illustrated in FIG. 1 and consume the substantially same rate of power in the operation. Thus, a first coil L of the voltage converting circuit 111a and a second coil L of the voltage converting circuit 111b have the substantially same magnitude of current flow, generating the substantially same magnitude of leakage magnetic fields. Hence, the configuration of FIG. 7 including the facing coils L enables effective offset of leakage magnetic fields between the voltage converting circuits 111a and 111b.

A third voltage converting circuit 111c feeds power voltage to the image processor 15, and a fourth voltage converting circuit 111d feeds power voltage to the image converter 17. In this context, the image processor 15 and the image converter 17 consume substantially equal rates of electrical power that are relatively high among individual electric components in the ultrasound diagnostic apparatus 1 during the operation. Thus, a third coil L in the voltage converting circuit 111c and a fourth coil L in the voltage converting circuit 111d have the substantially same magnitude of current flow, generating the substantially same magnitude of leakage magnetic fields. The configuration of FIG. 7 including the facing coils L enables an effective offset of leakage magnetic fields between the voltage converting circuits 111c and 111d.

In addition to the combination of the transmitter 12, the receiver 13, the image processor 15, and the image converter 17, any other combination of electrical components having substantially equal or similar power consumption may be employed which are supplied with the power voltage from the voltage converting circuits 111 partially offsetting leakage magnetic fields. For example, if the receiver 13 and the image processor 15 each include a single FPGA having the substantially same power consumption as the FPGA of the transmitter 12, the power voltage may be supplied to these two FPGAs from the two voltage converting circuits 111 partially offsetting leakage magnetic fields.

In FIG. 7, the magnetic fields M generated at the respective coils L of the voltage converting circuits 111a to 111g are parallel to the extending direction of the line 13a. Thus, the direction of the majority of induced magnetic fields generated by fluctuation in the leakage magnetic fields from the respective coils L of the voltage converting circuits 111a to 111g is orthogonal to the extending direction of the line 13a, thereby reducing the induced current generated by the induced electromotive force of the induced magnetic field in the line 13a. This can reduce the noise in ultrasound receiving signals generated by the leakage magnetic field.

In addition, the line 13a is provided in an area covering the farthest edge from a central line CL extending through the center of the board S (barycenter of the rectangle defining the board S in this context), and the respective coils L in the voltage converting circuits 111a to 111g are disposed remote from the line 13a relative to the central line CL so as to maximize the distance to the line 13a. This can reduce the induced magnetic field generated from the line 13a.

In FIG. 7, the magnetic field directions M from the coils L in all the voltage converting circuits 111 are parallel to the extending direction of line 13a. Alternatively, the magnetic field directions M from some voltage converting circuits 111 need not be parallel to the extending direction of line 13a. Such a configuration can also achieve a certain noise reduction effect. Although the entire line 13a is parallel to the magnetic field directions M from the respective voltage converting circuits 111 in FIG. 7, a portion of the line 13a need not be parallel to the magnetic field directions M. Such a configuration can also have a certain noise reduction effect.

In the present embodiment, the geometry of the coils L in the power supply 11 provided in the ultrasound diagnostic apparatus main body 10 has been described. Alternatively, the ultrasound probe 20 may include a power supply with a voltage converting circuit (in other words, the ultrasound probe 20 is integrated with the coils L) such that leakage magnetic fields are partially offset in the power supply.

(Modification)

A modification of the above-mentioned embodiments will now be described. The modification differs from the embodiments above in that one voltage converting circuit 111 includes two or more coils L. Differences from the embodiments above will now be described.

Figure 8:
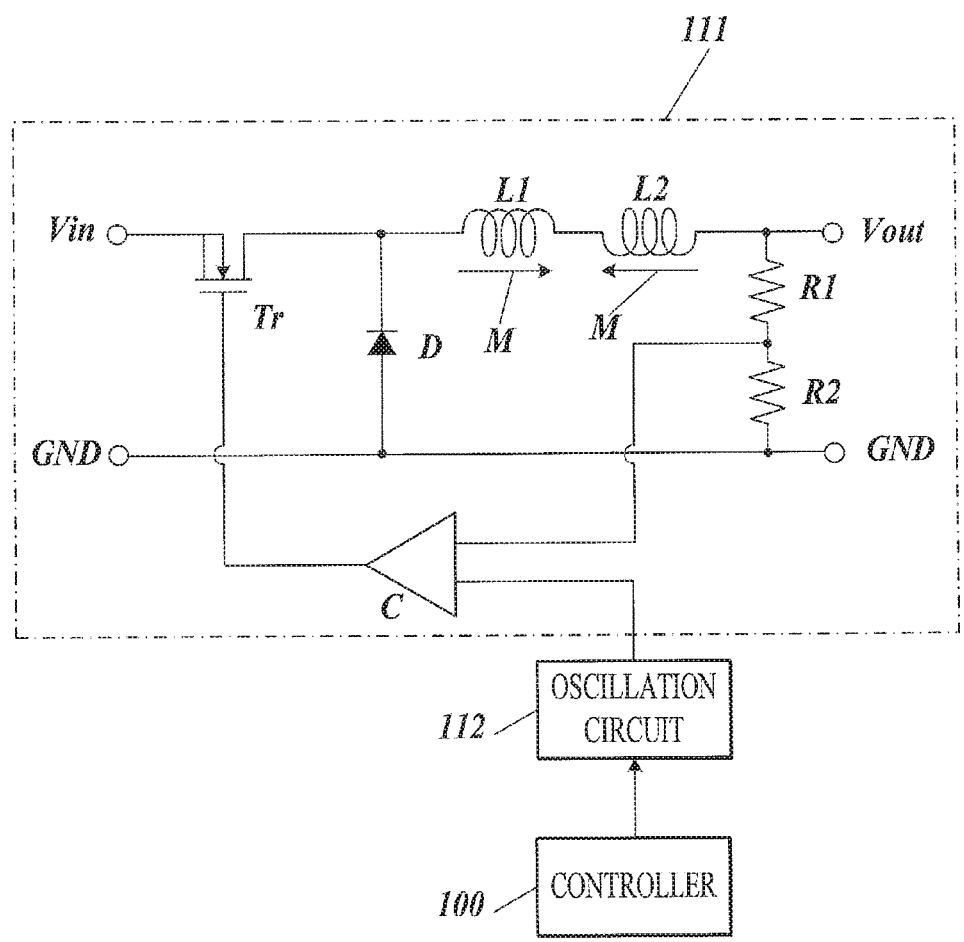
FIG. 8 illustrates the configuration and the operation of a voltage conversion circuit according to a modification.

FIG. 8 illustrates the configuration and operation of the voltage converting circuit 111 according to the modification. The modified voltage converting circuit 111 includes coils L1 and L2 connected in series and each having an aperture facing one another instead of the coil L in the voltage converting circuit 111 according to the embodiment above (FIG. 3A).

The winding direction of the coil L1 is reverse to that of the coil L2. The direction M of the magnetic field generated in the coil L1 is thus reversed to the direction M of the magnetic field generated in the coil L2 when current flows in the coils L1 and L2, thereby partially offsetting the leakage magnetic fields from the coils L1 and L2. Such a configuration can offset the leakage magnetic fields in the voltage converting circuit 111 of the modification, reducing the noise in ultrasound receiving signals.

It should be noted that multiple voltage converting circuits 111 may be disposed such that the leakage magnetic fields from at least one of the one coil L1 and the other coil L2 are further negated partially by the leakage magnetic fields from the coils L in other voltage converting circuits 111.

As described above, the ultrasound diagnostic apparatus 1 according to the present embodiment including the ultrasound probe 20 emitting ultrasound toward a subject and receiving the reflected waves from the subject and the display 19a for displaying an ultrasound image in response to the received signal, and further includes the power supply 11 comprising at least one voltage converting circuit 111 converting input voltage to a predetermined power voltage for output, the voltage converting circuit 111 comprising a plurality of coils L and the transistor Tr performing a switching operation for switching routes of current flowing in the coils L in response to a predetermined switching control signal, the voltage converting circuit 111 outputting the power voltage through the repeated switching operations under supply of the input voltage, where the coils L are disposed such that a leakage magnetic field in the vicinity of the aperture of at least one of the coils L is partially negated by leakage magnetic fields from one or more of the other coils L.

Such a configuration can partially offset leakage magnetic fields from the coils L in the power supply 11, reducing the noise caused by the leakage magnetic fields in ultrasound receiving signals. Thus, the quality of an ultrasound image displayed by the ultrasound diagnostic apparatus 1 can be maintained. In addition, multiple coils L are disposed such that magnetic fields are offset in the vicinity of the aperture, which has a high magnetic flux density, of the coil L, thereby effectively reducing leakage magnetic fields. Leakage magnetic fields can be reduced without complicated control of the power supply 11 such as control of the switching frequency of the voltage converting circuit 111, keeping the high quality of an ultrasound image. The effect of a reduction in leakage magnetic fields can be achieved without control of the switching frequency of the voltage converting circuit 111, enabling operation of the voltage converting circuit 111 at the frequency capable of highly effective power conversion, while maintaining the efficiency of the power supply 11 and the quality of an ultrasound image. The effect of a reduction in leakage magnetic fields can be acquired without a shield, preventing increase in the production costs of the ultrasound diagnostic apparatus 1.

The coils L are disposed such that the aperture of at least one of the coils L faces the aperture of one or more of the other coils L generating leakage magnetic fields for partially negating a leakage magnetic field in the vicinity of the aperture. Such a configuration can more effectively offset the leakage magnetic fields in the vicinity of the aperture, which has a high magnetic flux density, of the coil L, and thus more effectively reduce the leakage magnetic fields.

The at least one voltage converting circuit 111 comprises a plurality of voltage converting circuits 111 each provided with coils L. Such a configuration can facilitate reductions in leakage magnetic fields through the adjustment of the alignment of the coils L in the voltage converting circuits 111, preventing reduction in quality of an ultrasound image. For example, if each of the voltage converting circuits 111 is a single packaged component, alignment of the packaged component can facilitate reductions in leakage magnetic fields.

The controller 100, the oscillation circuit 112, and the comparator C (collectively referred to as a power controller) in the ultrasound diagnostic apparatus 1 supply switching control signals to the voltage converting circuits 111 for switching operation at the same frequency through the transistors Tr. In such a configuration, since the switching frequency and the phase of the circuits are common among the voltage converting circuits 111, the leakage magnetic fields from the coils L become large at the same time, effectively offsetting the leakage magnetic fields.

The voltage converting circuit 111 in the modification above includes at least two coils L, and the at least two coils L are disposed such that a leakage magnetic field in the vicinity of the aperture of one of the coils L is partially negated by leakage magnetic fields from one or more of the other coils L. Such a configuration can offset the leakage magnetic fields in the voltage converting circuit 111, providing flexibility in the geometry of the voltage converting circuits 111.

The coils L are disposed such that a leakage magnetic field in the vicinity of the aperture of at least one of the coils L is partially negated by leakage magnetic fields from two of the other coils L. Thus, even if leakage magnetic fields from the coils L differ in magnitude, combination of three or more coils L can effectively reduce the leakage magnetic fields.

The ultrasound diagnostic apparatus 1 further includes the receiver 13 receiving signals of ultrasound emitted from the ultrasound probe 20, and the transmitter 12 outputting driving signals for causing the ultrasound probe 20 to emit ultrasound, where the receiver 13 operates at the power voltage output from the voltage converting circuit 111a (a first voltage converting circuit), the transmitter 12 operates at the power voltage output from the voltage converting circuit 111b (a second voltage converting circuit), and a first coil in the voltage converting circuit 111a and a second coil in the voltage converting circuit 111b are disposed such that a leakage magnetic field in the vicinity of the aperture of the one coil is negated by a leakage magnetic field from the other coil. The voltage converting circuits 111a and 111b output the power voltage respectively to the receiver 13 and the transmitter 12 consuming the substantially same amount of power during the operation. Hence, the magnitude of the current flowing in the coils L, in other words, the magnitude of leakage magnetic fields from the coils L is substantially the same. As in the configuration above, the coils L are disposed such that leakage magnetic fields are offset between the voltage converting circuits 111a and 111b, resulting in effective reductions in leakage magnetic fields.

The ultrasound diagnostic apparatus 1 further includes the image processor 15 generating ultrasound image data in response to signals of ultrasound received by the ultrasound probe 20, and the image converter 17 converting the image data to image data conforming to a displaying mode of the display 19a, where the image processer 15 operates at the power voltage output from the voltage converting circuit 111c (a third voltage converting circuit), the image converter 17 operates at the power voltage output from the voltage converting circuit 111d (a fourth voltage converting circuit), and a third coil in the voltage converting circuit 111c and a fourth coil in the voltage converting circuit 111d are disposed such that a leakage magnetic field in the vicinity of the aperture of the third coil is partially negated by a leakage magnetic field from the fourth coil. The voltage converting circuits 111c and 111d output the power voltage respectively to the image processor 15 and the image converter 17 consuming the substantially same amount of power during the operation. Hence, the magnitude of the current flowing in the coil L, in other words, the magnitude of the leakage magnetic field from the coil L in the voltage converting circuit 111c is substantially the same as that of the voltage converting circuit 111d. As in the configuration above, the coils L are disposed such that leakage magnetic fields are offset between the voltage converting circuits 111c and 111d, resulting in effective reductions in leakage magnetic fields.

A portion of the line 13a for transmitting the received signals supplied to the receiver 13 is provided so as to be parallel to the magnetic field directions M generated in at least two of the coils L. In this configuration, the majority of the induced magnetic field directions generated by fluctuation in leakage magnetic fields from the coils L can be perpendicular to the extending direction of the line 13a, thereby reducing the induced current generated in the line 13a through the induced electromotive force of the induced magnetic field. This can result in an effective reduction in noise generated by the leakage magnetic field in ultrasound receiving signals, reliably preventing reduction of quality of an ultrasound image.

The at least one voltage converting circuit 111 is provided on the board S, and the coils L are provided such that the magnetic field directions M generated in the coils L are parallel to the board S. Such a configuration can allow the majority of magnetic field directions leaking from the apertures of the respective coils L to be parallel to the board S, facilitating the offset of leakage magnetic fields from the coils L.

The at least one voltage converting circuit 111 and the receiver 13 are provided on the board S, and the line 13a on the board S for transmitting the received signals supplied to the receiver 13 is provided in the area covering the farthest edge from the central line CL of the board S extending through the center of the board S, and the coils L are provided opposite the line 13a relative to the central line. This configuration can reduce the induced magnetic field generated in the line 13a due to leakage magnetic fields from the coils L, further reducing the noise generated in the ultrasound receiving signals.

According to the ultrasound diagnostic apparatus 1, the coils L are integrated with the ultrasound probe 20. Such a configuration can reduce the leakage magnetic field generated in the ultrasound probe 20.

The embodiments and modification above are mere examples, and the present invention may include any other modifications.

For example, any voltage converting circuit other than the structures in FIGS. 3A or 8 can be employed that converts voltages through repeated switching of routes for current flowing in the coils L. A boosting type of voltage converting circuit may thus be employed that converts input voltage to a voltage larger than the input voltage.

In the embodiments and modification above, multiple voltage converting circuits 111 is exemplified that operate at the same frequency in response to signals from the common oscillation circuit 112. Alternatively, the voltage converting circuits 111 may be independently operated and controlled at different frequencies.

In the embodiments and modification above, the duty ratio of switching control signals input through the gate of the transistor Tr in the voltage converting circuit 111 is converged to a predetermined value with the oscillation circuit 112 and the comparator C. Any other modification may also be employed. For example, switching control signals with the duty ratio predetermined in proportion to the magnitude of the input voltage and the magnitude of the power voltage to be output may be directly supplied to the transistor Tr by the controller 100. In this case, the controller 100 defines the power controller.

In the embodiments and modification above, the coils L is exemplified that are provided such that the magnetic fields M generated in the coils L are parallel to the board S. Any other modification may also be employed. For example, the coils L may be provided such that the magnetic field M intersects (typically is orthogonal to) the board S. A sheet coil may be layered on the board S or coils may be provided respectively in the same position on the two surfaces of the board S to partially offset the leakage magnetic fields from the coils.

In the embodiments and modification, the present invention is applied to the ultrasound diagnostic apparatus 1 including the ultrasound probe 20. Any other modification may also be employed. For example, the present invention may be applied to the ultrasound diagnostic apparatus main body 10, where the ultrasound probe 20 can be mounted to and dismounted from the ultrasound diagnostic apparatus main body 10.

Although embodiments of the present invention have been described and illustrated in detail, it is clearly understood that the same is by way of illustration and example only and not limitation, the scope of the present invention should be interpreted by terms of the appended claims.

Japanese Patent Application No. 2016-214791 filed on Nov. 2, 2016 including description, claims, drawings, and abstract the entire disclosure is incorporated herein by reference in its entirety.

The invention claimed is:

1. An ultrasound diagnostic apparatus comprising:
an ultrasound probe emitting ultrasound toward a subject and receiving reflected ultrasound from the subject;
a display for displaying an ultrasound image in response to a signal received by the ultrasound probe; and
a power supply including a plurality of coils and at least one voltage converting circuit converting input voltage to a predetermined power voltage for output,
wherein, the voltage converting circuit includes one or more coils among the plurality of coils and a switching element performing a switching operation for switching routes of current flowing in the coil in response to a predetermined switching control signal,
the voltage converting circuit outputs the power voltage through the repeated switching operations under supply of the input voltage, and
the plurlity of coils provided in the power supply are disposed such that a leakage magnetic field in a vicinity of an aperture of at least one of the coils is partially negated by a leakage magnetic field from one or more of the other coils.

2. The ultrasound diagnostic apparatus according to claim 1, wherein the coils are disposed such that the aperture of at least one of the coils faces the aperture of one or more of the other coils generating leakage magnetic fields for partially negating the leakage magnetic field in the vicinity of the aperture.

3. The ultrasound diagnostic apparatus according to claim 1, wherein the power supply includes a plurality of voltage converting circuits each provided with one of the coils.

4. The ultrasound diagnostic apparatus according to claim 3, further comprising a power controller supplying the predetermined switching control signal to each of the voltage converting circuits for the switching operation at a same frequency through the switching element.

5. The ultrasound diagnostic apparatus according to claim 1, wherein the voltage converting circuit includes two or more coils among the plurality of coils, and the two or more coils are disposed such that the leakage magnetic field in the vicinity of the aperture of one of the coils is partially negated by the leakage magnetic fields from one or more of the other coils.

6. The ultrasound diagnostic apparatus according to claim 1, wherein the coils are disposed such that the leakage magnetic field in the vicinity of the aperture of at least one of the coils is partially negated by the leakage magnetic fields from two of the other coils.

7. The ultrasound diagnostic apparatus according to claim 1, further comprising:
   a receiver receiving signals of ultrasound emitted from the ultrasound probe; and
   a transmitter outputting driving signals for causing the ultrasound probe to emit ultrasound; wherein
   the receiver operates at the power voltage output from a first voltage converting circuit;
   the transmitter operates at the power voltage output from a second voltage converting circuit different from the first voltage converting circuit; and
   a first coil in the first voltage converting circuit among the plurality of coils and a second coil in the second voltage converting circuit among the plurality of coils are disposed such that the leakage magnetic field in the vicinity of the aperture of the first coil is partially negated by the leakage magnetic field from the second coil.

8. The ultrasound diagnostic apparatus according to claim 1, further comprising:
   an image processer generating image data for an ultrasound image in response to signals of ultrasound received at the ultrasound probe; and
   an image converter converting the image data to image data conforming to a displaying mode of the display;
   wherein, the image processer operates at the predetermined power voltage output from a third voltage converting circuit;
   the image converter operates at the predetermined power voltage output from a fourth voltage converting circuit different from the third voltage converting circuit; and
   a third coil in the third voltage converting circuit among the plurality of coils and a fourth coil in the fourth voltage converting circuit among the plurality of coils are disposed such that the leakage magnetic field in the vicinity of the aperture of the third coil is partially negated by the leakage magnetic field from the fourth coil.

9. The ultrasound diagnostic apparatus according to claim 1, further comprising a receiver receiving signals of ultrasound emitted from the ultrasound probe, wherein at least a portion of a transmission route for the received signals supplied to the receiver is provided so as to be parallel to a direction of the magnetic fields generated in at least some of the coils.

10. The ultrasound diagnostic apparatus according to claim 1, wherein
    the at least one voltage converting circuit is provided on a predetermined board, and
    the coils are provided such that a direction of the magnetic fields generated in the coils are parallel to the board.

11. The ultrasound diagnostic apparatus according to claim 1, further comprising a receiver receiving signals of ultrasound emitted from the ultrasound probe, wherein
    the at least one voltage converting circuit and the receiver are provided on a predetermined board; and
    a transmission route on the board for the received signals supplied to the receiver is provided in an area covering a farthest edge from a predetermined central line of the board extending through a center of the board, and the coils are provided opposite of the transmission route relative to the central line.

12. The ultrasound diagnostic apparatus according to claim 1, further comprising the ultrasound probe wherein the coils are integrated with the ultrasound probe.

* * * * *